United States Patent [19]

McDonald

[11] Patent Number: 5,578,081
[45] Date of Patent: Nov. 26, 1996

[54] EYE MUSCLE RESPONSIVE ARTIFICIAL LENS UNIT

[75] Inventor: Henry H. McDonald, 65 N. Madison, Suite 305, Pasadena, Calif. 91101

[73] Assignees: Henry H. McDonald; William W. Haefliger, both of Pasadena, Calif.; a part interest

[21] Appl. No.: 544,976

[22] Filed: Oct. 30, 1995

Related U.S. Application Data

[63] Continuation-in-part of Ser. No. 423,216, Apr. 17, 1995, which is a continuation of Ser. No. 103,573, Aug. 9, 1993, abandoned, which is a continuation-in-part of Ser. No. 43,009, Apr. 5, 1993, Pat. No. 5,425,759, which is a continuation of Ser. No. 807,204, Dec. 16, 1991, Pat. No. 5,203,790, which is a continuation-in-part of Ser. No. 791,002, Nov. 12, 1991, Pat. No. 5,203,789.

[51] Int. Cl.⁶ ............................................. A61F 2/16
[52] U.S. Cl. ................................................. 623/6
[58] Field of Search .................................... 623/6

[56] References Cited

U.S. PATENT DOCUMENTS

| | | | |
|---|---|---|---|
| 4,198,714 | 4/1980 | Jensen | 623/6 |
| 4,414,694 | 11/1983 | Choyce | 623/6 |
| 4,441,217 | 4/1984 | Cozean, Jr. | 623/6 |
| 4,573,998 | 3/1986 | Mazzocco | 623/6 |
| 4,605,409 | 8/1986 | Kelman | 623/6 |
| 4,731,078 | 3/1988 | Stoy et al. | 623/6 |
| 4,769,035 | 9/1988 | Kelman | 623/6 |
| 4,786,445 | 11/1988 | Portnoy et al. | 623/6 |
| 4,790,846 | 12/1988 | Christ et al. | 623/6 |
| 4,813,957 | 3/1989 | McDonald | 623/6 |
| 4,833,890 | 5/1989 | Kelman | 623/6 |
| 4,834,751 | 5/1989 | Knight et al. | 623/6 |
| 4,840,627 | 6/1989 | Blumenthal | 623/6 |
| 4,842,602 | 6/1989 | Nguyen | 623/6 |
| 4,880,426 | 11/1989 | Ting et al. | 623/6 |
| 4,888,013 | 12/1989 | Ting et al. | 623/6 |
| 4,888,014 | 12/1989 | Nguyen | 623/6 |
| 4,894,062 | 1/1990 | Knight et al. | 623/6 |
| 4,932,970 | 6/1990 | Portney | 623/6 |
| 4,938,767 | 7/1990 | Ting et al. | 623/6 |
| 4,957,505 | 9/1990 | McDonald | 623/6 |
| 4,959,070 | 9/1990 | McDonald | 623/6 |
| 4,978,354 | 12/1900 | Van Gent | 623/6 |
| 5,030,231 | 7/1991 | Portney | 623/6 |
| 5,044,743 | 9/1991 | Ting | 623/6 |
| 5,203,789 | 4/1993 | McDonald | 623/6 |
| 5,203,790 | 4/1993 | McDonald | 623/6 |
| 5,217,464 | 6/1993 | McDonald | 606/107 |
| 5,395,378 | 3/1995 | McDonald | 623/6 |
| 5,476,514 | 12/1995 | Cumming | 623/6 |

*Primary Examiner*—Randy C. Shay
*Attorney, Agent, or Firm*—William W. Haefliger

[57] ABSTRACT

An artificial lens unit insertable into a capsular eye lens zone from which a natural lens has been removed, comprising the lens having a light refracting optical portion defining an axis, and consisting of plastic; the unit including haptics for positioning the lens in the capsular zone, the haptics extending at angles relative to a plane normal to the axis and passing through the lens; and the haptics' angles characterized in that the lens is displaced in the direction of the axis by the haptics in response to eye muscle constriction of the periphery of the capsular zone toward the axis.

15 Claims, 4 Drawing Sheets

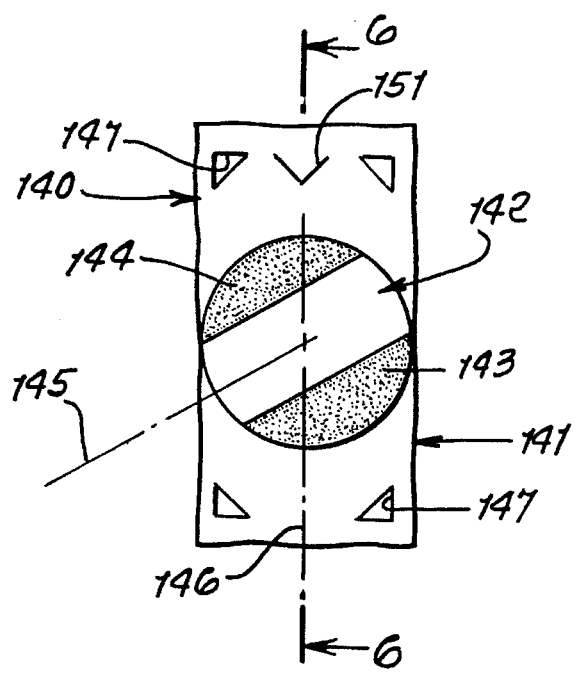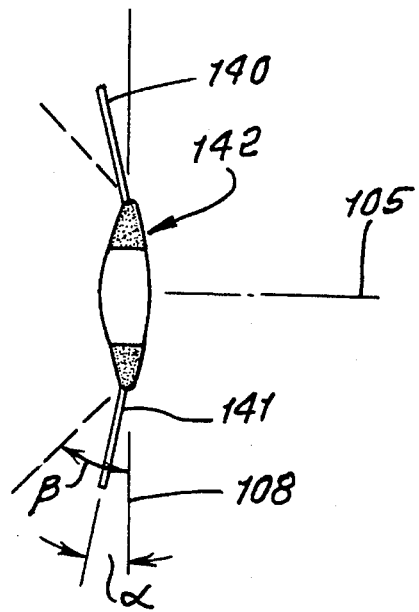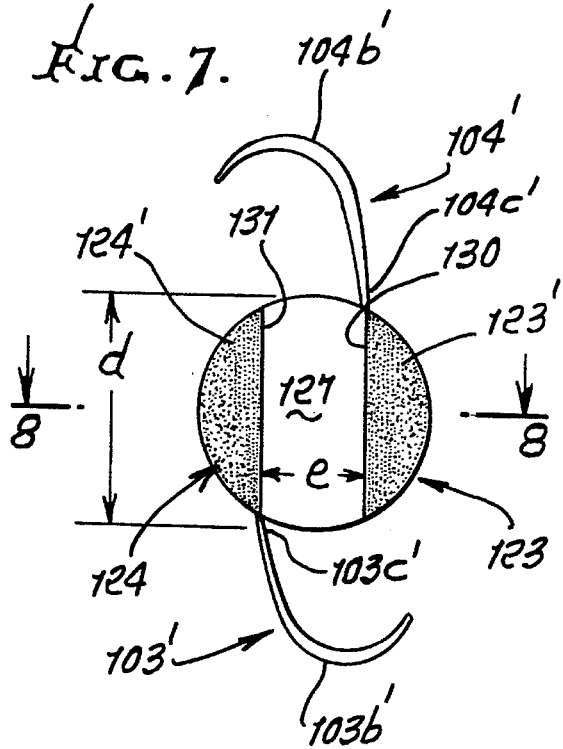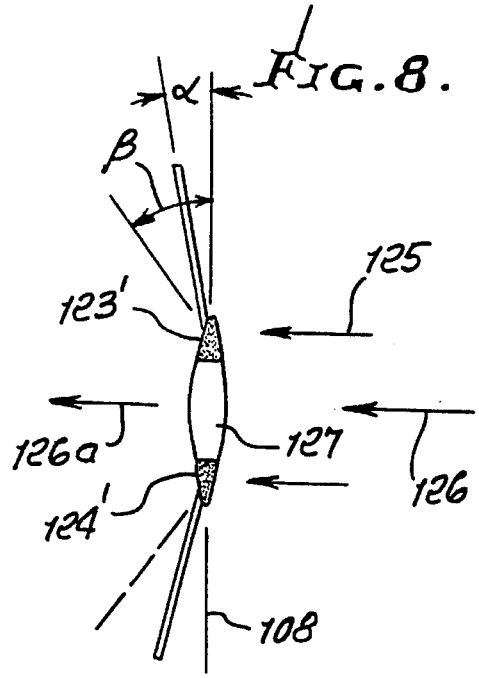

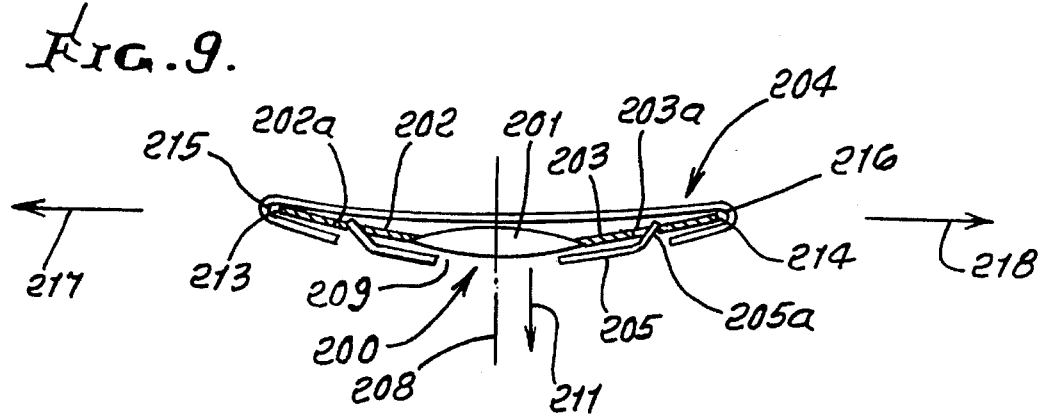
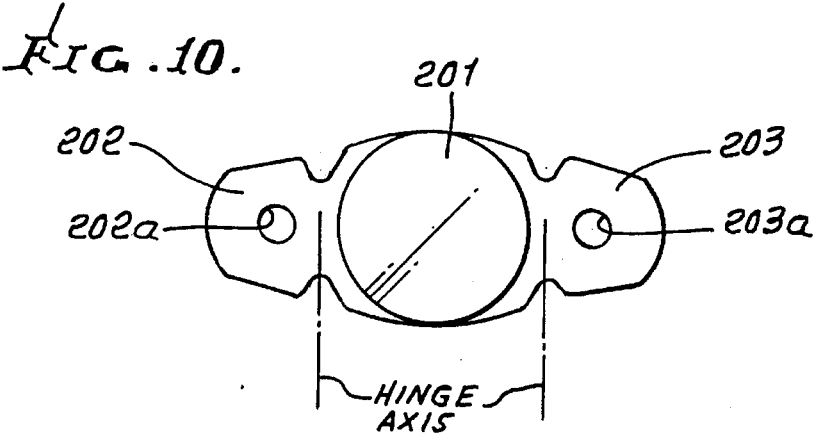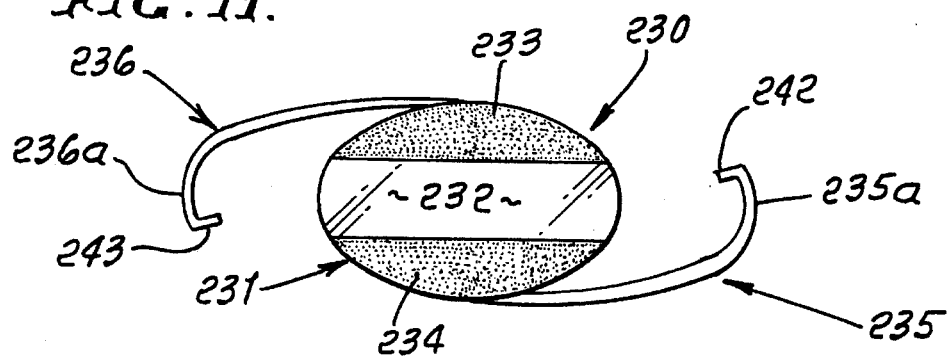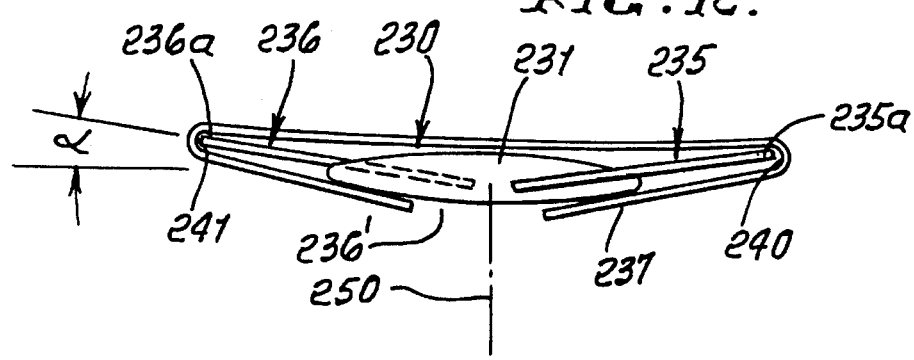

EYE MUSCLE RESPONSIVE ARTIFICIAL LENS UNIT

BACKGROUND OF THE INVENTION

This application is a continuation-in-part of prior U.S. application Ser. No. 08/423,216, filed Apr. 17, 1995, now allowed, which is a continuation of prior U.S. application Ser. No. 08/103,573, filed Aug. 9, 1993, now abandoned, which is a continuation-in-part of prior U.S. application Ser. No. 08/043,009, filed Apr. 5, 1993, now U.S. Pat. No. 5,425,759, which is a continuation of prior U.S. application Ser. No. 07/807,204, filed, Dec. 16, 1991, now U.S. Pat. No. 5,203,790, which is a continuation-in-part of prior U.S. application Ser. No. 07/791,002, filed Nov. 12, 1991, now U.S. Pat. No. 5,203,789, all of which are incorporated herein by reference.

This invention relates generally to method and apparatus for making an eye inserted artificial lens responsive to eye muscle contraction, for proper focusing; and to use of a lens having light ray occluding sections in this environment. There is need for improvements in artificial lenses, to be used for such purposes.

SUMMARY OF THE INVENTION

It is a major object of the invention to provide apparatus and method, meeting the above needs. Basically the invention is embodied in an artificial lens unit insertable into a capsular eye lens zone from which a natural lens has been removed, and comprises:

a) the lens having a light refracting optical portion defining an axis, and consisting of plastic, b) said unit including haptics for positioning the lens in the capsular zone, the haptics extending at angles relative to a plane normal to the axis and passing through the lens, and the haptics angles characterized in that the lens is displaced in the direction of the axis by the haptics in response to eye muscle constriction of the periphery of the capsular zone toward that axis.

Another object is to provide a lens and haptics unit, and wherein the haptics as viewed edgewise in the direction of said plane have substantially C-shape. Also, the haptics may extend at angles between 15° and 50° between the defined plane.

A further object is to provide such haptics which have integral connection to the lens, and which may hinge relative thereto, other portions of the haptics being sufficiently stiff to transmit lens deflection force to the lens. The haptics may have wire-like strand form, or may be tabular, as will appear; and they may contain eye tissue receiving openings to anchor the haptics against rotation. Their terminals are shaped to fit against inner edge extents of the capsular zone, to receive eye muscle transmitted force. The haptics are variably constrained inwardly toward the optical axis by the edge extents of said capsular zone, to variably and correspondingly displace the lens axially. Also the haptics may have increased thickness along their major lengths, to provide stiffness, and may have reduced thickness close to the lens, to provide for hinging.

The basic method of the invention includes the steps:

a) providing a plastic lens with a light refracting optical portion defining an axis, and b) providing lens haptics for positioning the lens in an eye capsular zone from which a natural lens has been removed, c) the haptics provided to extend at angles relative to a plane normal to the axis and passing through the lens, and characterized in that the lens is displaced in the direction of the axis by the haptics in response to eye muscle constriction of the periphery of the capsular zone toward the axis.

Also, the method may include positioning the lens and haptics in the capsular zone so that haptic angularity remains when the haptics peripheries engage interior edge extents of the capsular zone, whereby said haptics are variably constrained inwardly toward the axis by the inner edge extents of said capsular zone, to variably and correspondingly displace the lens axially, as for example to correctly focus light rays from an object onto the retina.

These and other objects and advantages of the invention, as well as the details of an illustrative embodiment, will be more fully understood from the following specification and drawings, in which:

DRAWING DESCRIPTION

FIG. 5 shows a lens unit having tabular haptics;

FIG. 6 is a section taken on lines 6—6 of FIG. 5;

FIG. 7 is a view like FIG. 1, showing a lens unit having occluded lens sections, and haptics with stiff and hinging sections;

FIG. 8 is a section taken on lines 8—8 of FIG. 7;

FIG. 9 is a side view of a modification;

FIG. 10 is a plan or frontal view of the FIG. 9 modification;

FIG. 11 is a frontal view of a further modification; and

FIG. 12 is a side view of the FIG. 11 modification.

DETAILED DESCRIPTION

Figure 1:
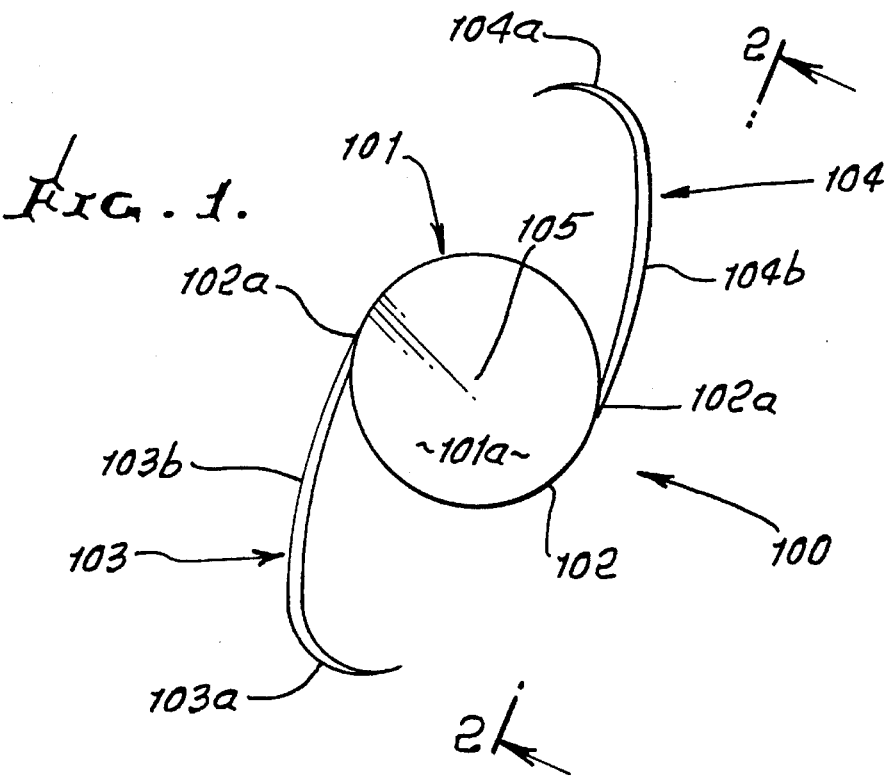
FIG. 1 is a frontal view of a lens unit.
Figure 2:
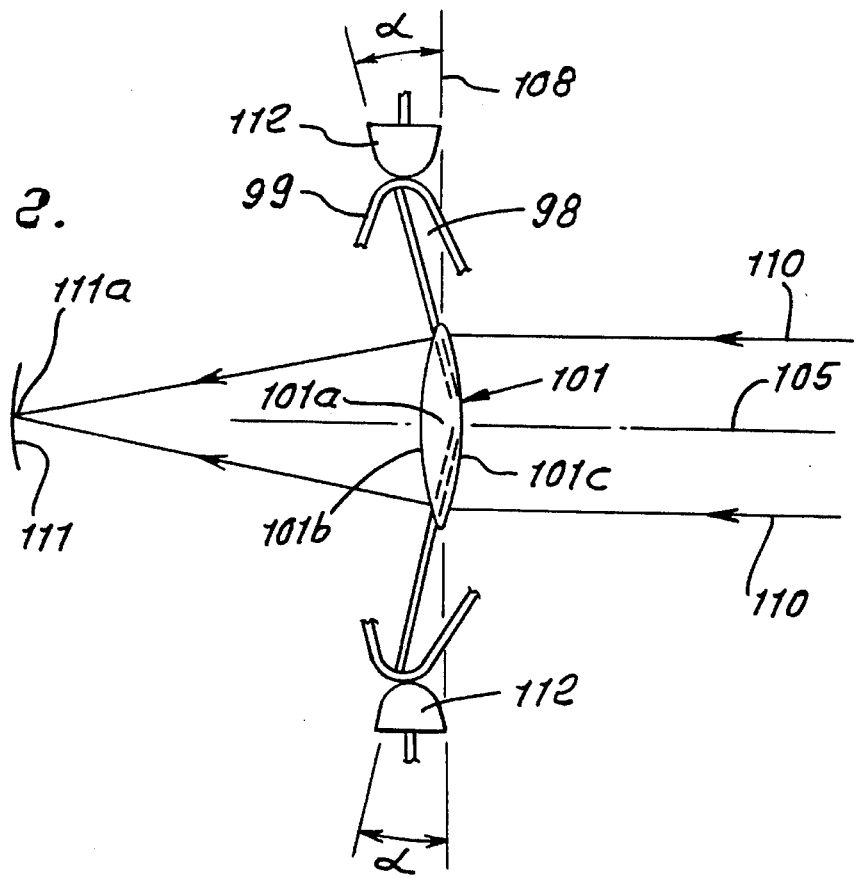
FIG. 2 is a section taken on lines 2—2 of FIG. 1, showing haptics angulation.
Figure 3:
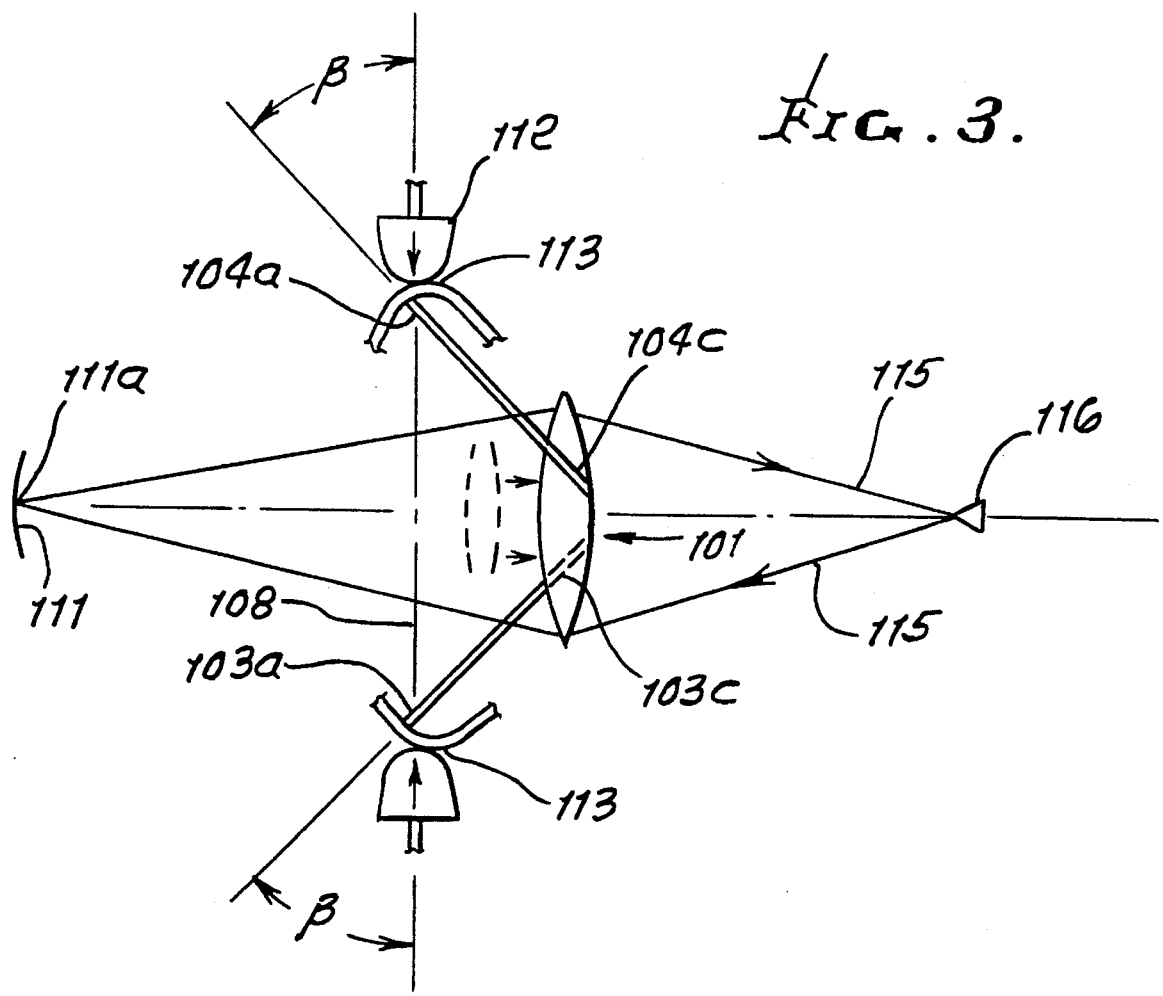
FIG. 3 is a view like FIG. 2, and showing haptics increased angulation, in response to cilia muscle contraction.

FIGS. 1–3 show a plastic lens unit 100; which may be sized for yieldably resilient folding and insertion into an eye zone 98 in a capsule 99 from which a cataractous material lens has been removed. See for example U.S. Pat. No. 4,803,957. The beadlike lens 101 of unit 100 may consist of silicone or equivalent material, and has light passing zone 101*a* between outwardly convex lens surfaces 101*b* and 101*c*. Attached to the lens as at locations 102*a* at circular periphery 102 are two, like, oppositely extending solid haptics 103 and 104. Loop type haptics may alternatively be employed. See the publication entitled "Simultaneously Endocapsular Implantation of Haptics and Optic Segment Using Cross-Action Folding Forceps" by Henry H. McDonald, M.D. An optical central axis is shown at 105.

In accordance with the invention, the C-shaped haptics are characterized as variably positioning the lens 101 along axis 105, in the eye, and within the capsule 99 which bounds the inserted artificial lens and haptics. The haptics extend at angles α relative to a plane 108 normal to axis 105, in FIG. 2, forming a shallow C-shape, as viewed. Parallel rays of light 110 are refracted by the lens to focus at point 111*a* at the wearer's retina 111.

Eye ciliary muscles 112 control contraction toward axis 105; and in FIG. 3 those muscles have contracted to deflect the periphery 113 of the capsule 99 toward axis 105. The outermost extents 103a and 104a of the haptics are deflected radially inwardly, and the haptics main extents 103b and 104b are sufficiently stiff to push or deflect the lens 101 bodily rightwardly in FIG. 3. Such deflection is sufficient to cause the lens to refract light rays 115 from an object 116 to again focus at point 111a at the wearer's retina. Such controlled lens deflection also corresponds to angle β of the haptics relative to plane 108, for the particular object location shown, as an example. Also, such lens deflection to obtain proper focusing is made possible by the initial angularity of the haptics, by their stiffness along their main extents 103b and 104b, and by hinging at haptic extents 103c and 104c closest to the lens. See for example the construction of the haptics 103' and 104' in FIG. 7, with thickened or widened main extents 103b' and 104b' for adequate column stiffening to transmit force toward the lens, and reduced thickness or width sections 103c' and 104c', to provide bendability or hinging relative to the lens, in response to ciliary muscle contraction.

Figure 4:
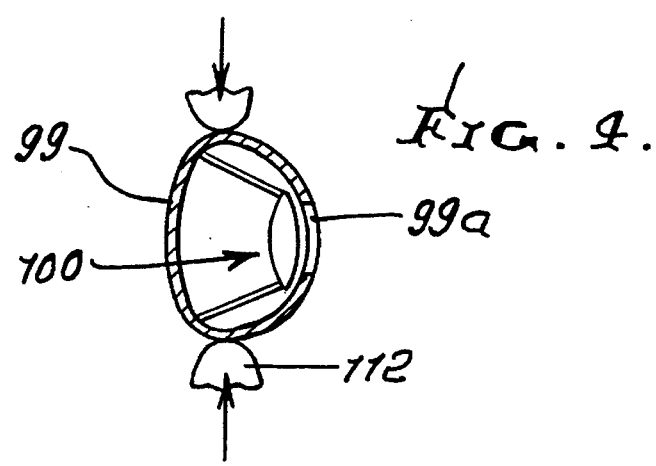
FIG. 4 shows an angulated lens unit within the eye lens capsule.

FIG. 4 shows the capsule 99 or "bag" surrounding the lens unit 100, and also deflected by the lens unit as in FIG. 3 position, due to ciliary muscle contraction. An insertion opening cut in the capsule appears at 99a.

FIGS. 7 and 8 show a modified lens that has two opposed peripheral segments 123 and 124 and which are characterized as light blocking. They may be internally darkened, or cloudy, or occluded, or the surfaces of the segments may be treated so as to be irregular, or occluded or darkened, to achieve light blocking effect. See light rays 125 in FIG. 8 blocked by 123 and 124, whereas light rays 126 incident on the lens light passing and refracting intermediate portion 127 are not blocked, and pass from the lens at 126a. Further, the segments 123 and 124 have substantially reduced thickness (de-bulking) over their major extents, relative to the thickness of clear lens 127 over its major extent. Note also that the two segments typically have substantially equal size and shape, and they extend adjacent the intermediate optics portion 127 along substantially linear and parallel borders 130 and 131 as seen in FIG. 7, such borders extending horizontally, as installed. Also, the segments 123 and 124 have generally convex outer edges 123' and 124', in the plane of the lens. Typical dimensions are as follows:

d≅5–8 mm.

e≅2 to 4 mm, where "d" is the diameter of the intermediate portion 127, and "e" is the spacing between the segments, borders 130 and 131 as seen in FIG. 7.

Note initial angularity α of the haptics relative to plane 108 corresponds to that discussed above, in FIG. 2; also the increased angularity β that corresponds to β in FIG. 3. It will be noted that the lens is deflectable to an infinite number of positions corresponding to an infinite range of haptics angularities, as referred to, and viewed object locations, under control of the eye muscles, to obtain desired refraction of light rays from objects, to the retina. The angularity α may vary between 15° and 50°.

FIGS. 5 and 6 show tabular haptics 140 and 141, of the general type disclosed in U.S. Pat. No. 5,203,790 to McDonald. They too have angularities α and β as seen in FIG. 6, relative to a plane 108 normal to optical axis 105. See also occluded segments 143 and 144 of the lens 142, and corresponding to segments 123 and 124 in FIG. 7. The axis 145 of clear lens 142 is angled at 45° relative to an axis or plane 146 bisecting the tabular haptics. Through openings 147 in the haptics 140 and 141 are adapted and positioned to receive eye tissue, or eye growth tissue, to anchor the lens unit in the capsule 99. V-shaped slits may be provided at 151 in the haptics, to provide further anchoring, as by reception of eye tissue.

In FIGS. 9 and 10, the lens unit 200 includes a plastic lens 201, and tabular haptics 202 and 203 projecting lengthwise oppositely. Each haptic contains a through opening 202a and 203a sized to receive a tissue flap formed by the surgeon by slitting the wall of the capsule 204. See flap 205a in wall 205. Not only is lens unit rotation about axis 208 thereby blocked, but the lens 201 is also prevented from extruding in direction 211 through the opening 209 initially cut in capsule wall 205 (that allows insertion of the lens unit into the capsule). Note also the peripheries 213 and 214 of the haptics nested in the inner peripheral grooves 215 and 216 formed by the capsule, to tension the capsule, in directions 217 and 218, the haptics then assuming angularities α as discussed above.

In FIGS. 11 and 12, the lens unit 230 includes a lens 231 having a clear transparent medial horizontal portion 232, and two occluded outer portions 233 and 234. The lens is elongated lengthwise, between the strand-like or wire-like haptics 235 and 236 angled at angles α as above. The lens can be elongated, as up to 6–8 mm., to resist extrusion through opening 236 formed in the wall 237 of the capsule 238 and through which unit 230 is inserted into the capsule interior. Wire-like haptics 235 and 236 have terminal portions 235a and 236a that nest in the internal peripheral grooves 240 and 241 formed by the capsule. In-turned protrusions or tangs 242 and 243 on the terminal portions of the haptics are adapted to project and quickly attach to eye tissue, to resist lens unit rotation about optical axis 250, in unit installed position. Such anchored protrusions also resist extrusion of the lens through the opening 236'. The closer to the tab periphery or peripheries that the holes 236' are located, the sooner they will be penetrated by eye tissue, i.e. "scarify".

In FIGS. 9–12, all haptics are typically angulated, as at angles α referred to above, to be moved axially as eye muscles expand and contract.

I claim:

1. An artificial lens unit including a lens insertible into a capsular eye lens zone from which a natural lens has been removed, comprising, in combination, a) the lens having a light refracting optical portion defining an axis, and consisting of plastic, b) said unit including substantially C-shaped, filamentary haptics for positioning said lens in said capsular zone, said haptics extending at angles relative to a plane normal to said axis and passing through said lens, and said haptics' angles characterized in that said lens is displaced in the direction of said axis by said haptics in response to eye muscle constriction of the periphery of said capsular zone toward said axis, c) said haptics having outwardly convex arcuate outermost extents that define free terminals, and extend inwardly, said haptics having hinge connection to the lens and tangentially merging with the lens, and said haptics extend at angles between 15° and 50° relative to said plane.

2. The lens unit of claim 1 wherein said lens and said haptics, as viewed edgewise in the direction of said plane, have substantially a C-shape.

3. The lens unit of claim 1 wherein said haptics are integral with said lens, at edge portions thereof.

4. The lens unit of claim 1 wherein said lens has oppositely facing convex surfaces.

5. The combination of claim 1 wherein the haptics have thickness that is small proximate said hinge connection, and that is larger than the thickness proximate said hinge connection along major lengths thereof.

6. The lens unit of claim 1 wherein said lens has a length is elongated lengthwise and has a width smaller than said length.

7. The lens unit of claim 1 wherein said lens has a clear transparent medial zone, and is light-occluding outwardly of said medial zone.

8. The lens unit of claim 7 wherein said lens has a length, medial zone is elongated, along the length of the lens.

9. The lens unit of claim 7 wherein said clear medial zone has length between about 5 and 8 mm., and has width between 2 and 4 mm.

10. A method of providing for variable focal point positioning of the artificial lens unit of claim 1 in the eye that includes providing the lens unit of claim 1 and inserting the claim 1 lens unit in and positioning it in said eye capsular eye lens zone.

11. The method of claim 10 wherein said haptics terminals are fitted against interior edge extents of said capsular zone.

12. The method of claim 11 wherein said haptics are variably constrained inwardly toward said axis by eye muscle induced movement of said edge extents of said capsular zone, to variably and correspondingly displace the lens axially.

13. The method of claim 11 wherein said haptics have sideward protrusions operable to engage eye tissue and resist lens unit rotation.

14. A method of providing for variable focal point positioning of an artificial lens in the eye, which includes a) providing a plastic lens with a light refracting optical portion defining a axis, and b) providing filamentary lens haptics having respective hinge connections to the lens at locations of tangential merging with the lens for positioning said lens in an eye capsular zone from which a vertical lens has been removed, c) and including placing the lens and haptics in said eye capsular zone, and said haptics provided to extend at angles relative to a plane normal to said axis and passing through said lens, and characterized in that said lens is displaced in the direction of said axis by said haptics in response to eye muscle constriction of the periphery of said capsular zone toward said axis, thereby to maintain light ray focusing and the eye retina.

15. The method of claim 14 including positioning said lens and haptics in said capsular zone so that said haptic angularity remains when the haptics peripheries engage interior edge extents of said capsular zone, whereby said haptics are variably constrained inwardly toward said axis by said edge extents of said capsular zone to variably and correspondingly displace the lens axially, in response to said eye muscle constriction of the periphery of said capsular zone toward said axis.

* * * * *